United States Patent [19]

Clemence et al.

[11] Patent Number: 4,735,951
[45] Date of Patent: Apr. 5, 1988

[54] NOVEL 4-HYDROXY-3-QUINOLINE-CARBOXYLATES HAVING ANALGESIC AND ANTI-INFLAMMATORY ACTIVITY

[75] Inventors: Francois Clemence, Paris; Odile Le Martret, both of Paris; Françoise Delevallee, Fontenay-sous-Bois, all of France

[73] Assignee: Roussel Uclaf, Paris, France

[21] Appl. No.: 790,064

[22] Filed: Oct. 22, 1985

[30] Foreign Application Priority Data

Oct. 30, 1984 [FR] France ................... 84 16573

[51] Int. Cl.⁴ ............... A61K 31/47; C07D 215/56
[52] U.S. Cl. ..................... 514/312; 514/256; 546/89; 546/309; 546/156; 548/195
[58] Field of Search ........... 546/156; 514/312, 256; 544/322

[56] References Cited

U.S. PATENT DOCUMENTS 4,486,438  12/1984  Clemence et al. .......... 546/156 X

FOREIGN PATENT DOCUMENTS 3320102  12/1983  Fed. Rep. of Germany .
2123817   2/1984  United Kingdom ............ 546/156

Primary Examiner—Donald G. Daus
Assistant Examiner—Diana G. Rivers
Attorney, Agent, or Firm—Bierman and Muserlian

[57] ABSTRACT

Novel optical isomers and racemates of 4-hydroxy-3-quinoline-carboxylates of the formula

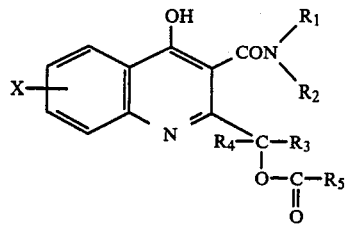

wherein X is in the 5-, 6-, 7- or 8-position and is selected from the group consisting of hydrogen, halogen, alkyl of 1 to 5 carbon atoms, alkoxy of 1 to 4 carbon atoms, —CF₃, —SCF₃ and —OCF₃, R₁ is selected from the group consisting of hydrogen and alkyl of 1 to 4 carbon atoms, R₂ is selected from the group consisting of thiazolyl, 4,5-dihydrothiazolyl, pyridinyl, oxazolyl, isoxazolyl, imidazolyl, pyrimidyl and tetrazolyl all optionally substituted with alkyl of 1 to 4 carbon atoms and phenyl substituted with at least one member of the group consisting of —OH, alkyl and alkoxy of 1 to 4 carbon atoms, —CF₃, —NO₂ and halogen, R₃ and R₄ are individually selected from the group consisting of hydrogen, alkyl of 1 to 4 carbon atoms and aryl, R₅ is selected from the group consisting of aryl of 6 to 14 carbon atoms, heteroaryl of 3 to 14 carbon atoms, alkyl of 1 to 14 carbon atoms, alkyl substituted with —NH₂, —NHAlk or

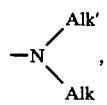

alkenyl of 2 to 6 carbon atoms, alkenyl of 2 to 6 carbon atoms substituted with aryl of 6 to 14 carbon atoms, Alk and Alk' are alkyl of 1 to 6 carbon atoms and their non-toxic, pharmaceutically acceptable acid addition salts with the proviso that when X is 8-CF₃, R₁ and R₃ are hydrogen, R₂ is 2-thiazolyl, R₄ is methyl, R₅ is not methyl having analgesic and anti-inflammatory activity.

21 Claims, No Drawings

NOVEL 4-HYDROXY-3-QUINOLINE-CARBOXYLATES HAVING ANALGESIC AND ANTI-INFLAMMATORY ACTIVITY

STATE OF THE ART

U.S. Pat. No. 4,486,438 describes related 4-hydroxy-3-quinoline-carboxylic acid derivatives.

OBJECTS OF THE INVENTION

It is an object of the invention to provide the novel compounds of formula I and their non-toxic, pharmaceutically acceptable acid addition salts and a process for their preparation.

It is another object of the invention to provide novel analgesic and anti-inflammatory compositions and a method of relieving pain and inflammation in warm-blooded animals.

These and other objects and advantages of the invention will become obvious from the following detailed description.

THE INVENTION

The novel compounds of the invention are optical isomers and racemates of 4-hydroxy-3-quinoline-carboxylates of the formula

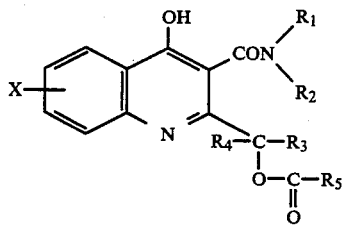

wherein X is in the 5-, 6-, 7- or 8-position and is selected from the group consisting of hydrogen, halogen, alkyl of 1 to 5 carbon atoms, alkoxy of 1 to 4 carbon atoms, —$CF_3$, —$SCF_3$ and —$OCF_3$, $R_1$ is selected from the group consisting of hydrogen and alkyl of 1 to 4 carbon atoms, $R_2$ is selected from the group consisting of thiazolyl, 4,5-dihydrothiazolyl, pyridinyl, oxazolyl, isoxazolyl, imidazolyl, pyrimidyl and tetrazolyl all optionally substituted with alkyl of 1 to 4 carbon atoms and phenyl and phenyl substituted with at least one member of the group consisting of —OH, alkyl and alkoxy of 1 to 4 carbon atoms, —$CF_3$, —$NO_2$ and halogen, $R_3$ and $R_4$ are individually selected from the group consisting of hydrogen, alkyl of 1 to 4 carbon atoms and aryl, $R_5$ is selected from the group consisting of aryl of 6 to 14 carbon atoms, heteroaryl of 3 to 14 carbon atoms, alkyl of 1 to 14 carbon atoms, alkyl substituted with —$NH_2$, —NHAlk or

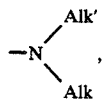

alkenyl of 2 to 6 carbon atoms, alkenyl of 2 to 6 carbon atoms substituted with aryl of 6 to 14 carbon atoms, Alk and Alk' are alkyl of 1 to 6 carbon atoms and their non-toxic, pharmaceutically acceptable acid addition salts with the proviso that when X is 8-$CF_3$, $R_1$ and $R_3$ are hydrogen, $R_2$ is 2-thiazolyl, $R_4$ is methyl, $R_5$ is not methyl.

When X is halogen, it is preferably chlorine and when X is alkyl, it is preferably methyl, ethyl, n-propyl, n-butyl, n-pentyl, isopropyl or isobutyl. When X is alkoxy, it is preferably methoxy, ethoxy or n-propoxy.

When $R_1$ is alkyl, it is preferably methyl or ethyl. When $R_2$ is heterocyclic substituted by alkyl, it is preferably a heterocyclic substituted by methyl or ethyl. When $R_2$ is substituted phenyl, it is preferably phenyl substituted by at least one radical chosen from the group consisting of hydroxy, methyl, ethyl, methoxy, ethoxy, trifluoromethyl, nitro and chlorine.

When $R_3$ is alkyl, it is preferably methyl, ethyl, propyl, isopropyl, butyl or isobutyl. When $R_3$ is aryl, it is preferably phenyl or naphthyl.

When $R_4$ is alkyl, it is preferably methyl, ethyl, propyl, isopropyl, butyl or isobutyl. When $R_4$ is aryl, it is preferably phenyl or naphthyl.

When $R_5$ is alkyl, it is preferably methyl, ethyl, propyl, isopropyl, butyl, isobutyl or tertbutyl. When $R_5$ is alkenyl, it is preferably vinyl, propenyl, butenyl or buta-1,3-dienyl. When $R_5$ is aryl or alkenyl substituted by aryl, aryl is preferably phenyl or naphthyl. When $R_5$ is heteroaryl, it is preferably a pyridyl.

Examples of suitable acids for the acid addition salts are mineral acids such as hydrochloric acid, hydrobromic acid, sulfuric acid and phosphoric acid, as well as sulfonic acid such as the alkyl or arylsulfonic acids, for example, methanesulfonic or p-toluene sulfonic acid.

Among the preferred compounds of formula I are those wherein X is is in 8-position, especially when X is trifluoromethyl as well as their acid addition salts and those wherein $R_1$ is hydrogen atom and those wherein $R_2$ is thiazolyl as well as their acid addition salts.

Other preferred compounds of the invention are those of formula I wherein $R_3$ is hydrogen, those wherein $R_4$ is ethyl and $R_5$ is selected from the group consisting of alkyl of 1 to 4 carbon atoms and alkyl of 1 to 4 carbon atoms substituted by an amino radical as well as their acid addition salts.

· Specific preferred compounds of the invention are: 2-[1-(1-oxopropoxy)-propyl]-4-hydroxy-N-(2-thiazolyl)-8-(trifluoromethyl)-3-quinoline carboxamide, in racemic or optically active form, 2-[1-(1-oxobutoxy)-propyl]-4-hydroxy-N-(2-thiazolyl)-8-(trifluoromethyl)-3-quinoline carboxamide, in racemic or optically active form and, 2-[1-(1-oxo-2-aminoethoxy)-propyl]-4-hydroxy-N-(2-thiazolyl)-8-(trifluoromethyl)-3-quinoline carboxamide, in racemic or optically active form and their non-toxic, pharmaceutically acid addition salts.

The novel process of the invention for the preparation of compounds of formula I comprises reacting a compound of the formula

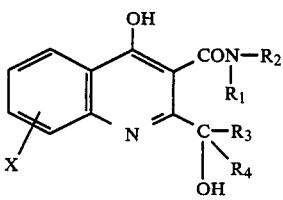

wherein X, $R_1$, $R_2$, $R_3$ and $R_4$ are defined as above with an acid of the formula

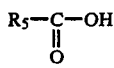

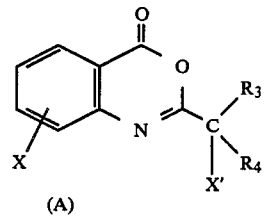
(A)

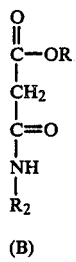
(B)

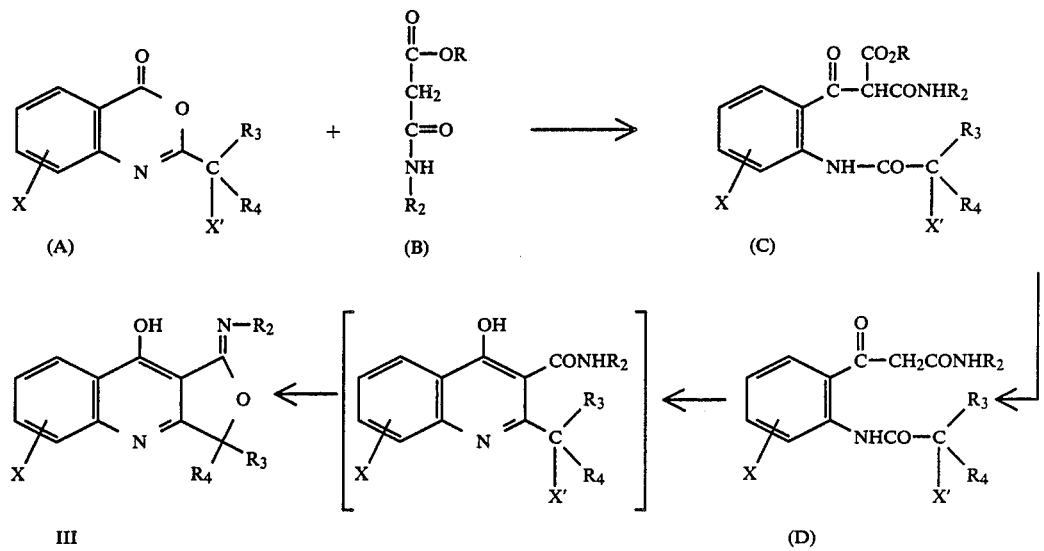

scribed in that patent. They can also be prepared by the process described in the European Application No. 141,713 illustrated as follows:

to obtain the corresponding compound of formula I which, if desired, is submitted to the action of an acid to form its acid addition salt.

In a preferred mode of the process, the reaction is effected in the presence of dicyclohexyl-carbodiimide and 4-dimethylamino-pyridine in an organic solvent and when $R_5$ is alkyl substituted by amino, an acid is used in which the amino is blocked and the freeing of the amino after esterification is effected by action of an acid. When it is desired to prepare an optically active product of formula I, there is used at the start an alcohol which is first resolved by the intermediary of an optically active acid leading to a mixture of esters which are separated by usual methods such as by crystallization or chromatography.

The products of formula II are described in European Patent Application No. 84-402074.3 published under No. 141713.

In a modification of the process of the invention for compounds of formula I wherein $R_1$ is hydrogen, a compound of the formula

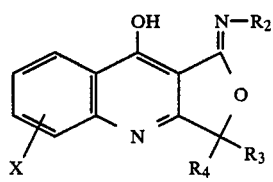
III wherein X, $R_2$, $R_3$ and $R_4$ are defined as above is reacted with an acid of the formula

to obtain a compound of formula I which, if desired, is submitted to the action of an acid to form its acid addition salt.

The compounds of formula III correspond to products of formula XII claimed in the Belgian Pat. No. 896,941 and they can be prepared by the process de- In the products of formulae A, B, C, D and III, X, $R_2$, $R_3$ and $R_4$ have the above definitions, X' is halogen and R is alkyl of 1 to 8 carbon atoms.

In a preferred mode of the process of the invention, the reaction between the compound of formula III and the acid $R_5COOH$ is carried out at a temperature between 100° and 150° C., or if the case arises, at reflux of the acid.

The analgesic and anti-inflammatory compositions of the invention are comprised of an analgesically and anti-inflammatorily effective amount of at least one compound of formula I and their non-toxic, pharmaceutically acceptable acid addition salts and an inert pharmaceutical carrier or excipient. The compositions may be in the form of tablets, dragees, gelules, granules, suppositories, injectable solutions or suspensions, pomades, creams, gels and aerosol preparations formed in the usual fashion.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants and emulsifiers and preservatives.

The compositions are useful for the treatment of muscular, articular or nervous pain, dental pain, rhumatismatic affections, zona, and migraines as well as a complementary treatment for infections and feverish states.

The compositions are also useful for the treatment of degenerative inflammatory maladies such as oesteoarthrosis, various collagen diseases (tendinitis, etc.), rheumatic maladies (rheumatoid polyarthritis, ankylosing spondylarthritis), as well as the treatment of other maladies of auto-immune nature such as disseminated erythematous lupus, glomerulonephritis, multiple sclerosis.

As compared to the compounds of formula II described in European Application No. 141,713, the compounds of the present invention and particularly those of Examples 2, 6 and 7 have a superior antiarthritic activity and the compounds of Examples 6 and 7 are well tolerated by the gastric system.

Preferred compositions of the invention are those wherein the active ingredient is selected from the group consisting of 2-[1-(1-oxopropoxy)-propyl]-4-hydroxy-N-(2-thiazolyl)-8-(trifluoromethyl)-3-quinoline carboxamide, in racemic or optically active form, 2-[1-(1-oxobutoxy)-propyl]-4-hydroxy-N-(2-thiazolyl)-8-trifluoromethyl)-3-quinoline carboxamide, in racemic or optically active form and, 2-[1-(1-oxo-2-aminoethoxy)-propyl]-4-hydroxy-N-(2-thiazolyl)-8-(trifluoromethyl)-3-quinoline carboxamide, in racemic or optically active forms, and their non-toxic, pharmaceutically acceptable acid addition salts.

The novel method of the invention for relieving pain and inflammation in warm-blooded animals, including humans, comprises administering to warm-blooded animals an analgesically and anti-inflammatorily effective amount of at least one compound of formula I and its non-toxic, pharmaceutically acceptable salts. The compounds may be administered orally, rectally, parenterally or topically to the skin or mucous. The usual effective dose is dependent on the specific compound and the method of administration, and the conditions treated and may be 0.25 to 25 mg/kg per day in the adult by oral route.

In the following examples there are described several preferred embodiments to illustrate the invention. However, it should be understood that the invention is not intended to be limited to the specific embodiments.

EXAMPLE 1

2-(1-acetyloxypropyl)-4-hydroxy-N-(2-thiazolyl)-8-trifluoromethyl-3-quinoline-carboxamide A suspension of 1 g of 1,3-dihydro-3-ethyl-1-[2-thiazolyl)-imino]-5-(trifluoromethyl)-furo-[3,4-b]-quinolin-9-ol (product prepared in Belgian Pat. No. 896,941) in 20 ml of acetic acid was refluxed for 90 minutes and the solution obtained was cooled and poured into 20 ml of water. After separating, washing and drying, 926 mg of 2-(1-acetyloxypropyl)-4-hydroxy-N-(2-thiazolyl)-8-trifluoromethyl-3-quinoline-carboxamide were obtained which was purified in refluxing ethyl acetate and was then cooled and separated to obtain 712 mg of the said product melting at 245° C.

EXAMPLE 2

4-hydroxy-2-[1-(1-oxopropoxy)-propyl]-N-(2-thiazolyl)-8-(trifluoromethyl)-3-quinoline carboxamide A suspension of 3 g of 1,3-dihydro-3-ethyl-1-[(2-thiazolyl)-imino]-5-(trifluoromethyl)-furo-[3,4-b]-quinolin-9-ol in 60 ml of propionic acid was held in a bath at 100°–110° C. for 2 hours and 50 minutes and the solution obtained was cooled and poured into 600 ml of water. After separating and washing with water, 2.5 g of product were obtained which was purified by crystallization from 40 ml of ethyl acetate. The crystals were cooled and recovered by filtration to obtain 1.7 g of 4-hydroxy-2-[1-(1-oxopropoxy)-propyl]-N-(2-thiazolyl)-8-(trifluoromethyl)-3-quinoline carboxamide melting at 216° C.

EXAMPLE 3

2-(1-acetyloxy-2-methylpropyl)-4-hydroxy-N-(2-thiazolyl)-8-trifluoromethyl-3-quinoline carboxamide

STEP A:
2-(1-chloro-2-methylpropyl)-8-(trifluoromethyl)-4H-3,1-benzoxazin-4-one 10.25 g of 2-amino-3-trifluoromethyl benzoic acid in 20 ml of toluene and 18.6 g of 2-chloro-3-methyl butanoyl chloride (prepared by J. Org. Chem., Vol. 40, p. 3420 (1975)) were mixed together, and the procedure of Example 10 of Belgian Patent No. 896,941 was followed for the preparation of 11.9 g of 2-(1-chloro-2-methylpropyl)-8-(trifuoromethy)-4H-3,1-benzoxazin-4-one melting at 78°–80° C.

STEP B:
3-isopropyl-1,3-dihydro-1-[(2-thiazolyl)-imino]-5-(trifluoromethyl)-furo-[3,4-b]-quinolin-9-ol 10.6 g of N-(2-thiazolyl)-acetamide, 325 ml of tetrahydrofuran and 106 ml of n-butyllithium in hexane titrating 1.4M and 11.4 g of 2-(1-chloro-2-methylpropyl)-8-(trifluoromethyl)-4H-3,1-benzoxazin-4-one of Step A in solution in 80 ml of tetrahydrofuran were reacted by the procedure of Step A of Example 6 of Belgian Pat. No. 896,941 to obtain 13.8 g of 2-[(2-chloro-1-oxo-3-methylbutyl)-amino]-β-oxo-N-(2-thiazolyl)-3-(trifluoromethyl)-benzene propanamide melting at 186° C.

11.65 g of the latter product in 200 ml of tetrahydrofuran and 3.8 g of 4-dimethylaminopyridine were refluxed for 16 hours and the tetrahydrofuran was eliminated under reduced pressure. 200 ml of water were added to the residue, and the pH was adjusted to 1–2 with N hydrochloric acid addition. After separating, washing with water and drying under reduced pressure at 100° C., 10.2 g of 3-isopropyl-1,3-dihydro-1-[(2-thiazolyl)-imino]-5-(trifluoromethyl)-furo-[3,4-b]-quinolin-9-ol melting at 246° to 248° C. were obtained.

STEP C:
2-(1-acetyloxy-2-methylpropyl)-4-hydroxy-N-(2-thiazolyl)-8-trifluoromethyl-3-quinoline carboxamide 10 g of product of Step B in 200 ml of acetic acid were refluxed for 57 hours and the solution was allowed to return to ambient temperature. Then, 200 ml of water were added followed by filtration. The orange product was washed with water and then was dissolved in a mixture of 250 ml of ethyl acetate and 500 ml of tetrahydrofuran. The mixture was dried and 1 g of active carbon was added. After filtering and concentrating to dryness under reduced pressure, 8.3 g of residue were obtained which was crystallized from 240 ml of ethyl acetate. The crystals were filtered hot, cooled, separated, dried under reduced pressure at 40° C. for 16 hours. 5.3 g of expected product were obtained, melting at 242° C.

EXAMPLE 4

4-hydroxy-2-[2-methyl-1-(1-oxopropoxy)-propyl]-N-(2-thiazolyl)-8-trifluoromethyl-3-quinoline carboxamide A suspension of 10 g of the compound of Step A of Example 3 in 200 ml of propionic acid was refluxed for 10 hours and then allowed to return to ambient temperature. 200 ml of water were added and then, after filtering and washing with water, the residue was dissolved in a mixture of 300 ml of ethyl acetate and 500 ml of tetrahydrofuran. After drying, filtering and concentrating to dryness under reduced pressure, 8.1 g of product were obtained which was crystallized from 90 ml of ethyl acetate. The crystals were filtered hot, separated, dried for 16 hours under reduced pressure at ambient temperature to obtain 5.5 g of 4-hydroxy-2-[2-methyl-1-(1-oxopropoxy)-propyl]-N-(2-thiazolyl)-8-trifluoromethyl-3-quinoline carboxamide melting at 222° C.

EXAMPLE 5

4-hydroxy-2-[1-(1-oxopropoxy)-propyl]-N-(2-thiazolyl)-8-trifluoromethyl-3-quinoline carboxamide 1.24 g of dicyclohexylcarbodiimide were added to a suspension of 2 g of 4-hydroxy-2-(1-hydroxypropyl)-N-(2-thiazolyl)-8-trifluoromethyl-3-quinoline carboxamide [prepared as in Step C of Example 10 of Belgian Patent No. 896,941] and 0.4 ml of propionic acid in 20 ml of methylene chloride. After stirring for 5 minutes, 0.30 g of 4-dimethylamino-pyridine were added and the mixture stood for an hour with stirring at ambient temperature. The dicyclohexylurea formed was filtered off and the organic phase was washed with N hydrochloric acid, then with an aqueous solution of sodium bicarbonate, then with water, followed by drying and concentrating to dryness under reduced pressure. The residue was taken up in 15 ml of ether, filtered, dried under reduced pressure to obtain 2.2 g of 4-hydroxy-2-[1-(1-oxopropoxy)-propyl]-N-(2-thiazolyl)-8-trifluoromethyl-3-quinoline carboxamide melting at 216° C. which was identical to that obtained in Example 2.

EXAMPLE 6

1-[4-hydroxy-3-[(2-thiazolylamino)-carbonyl]-8-(trifluoromethyl)-2-quinolinyl]-propyl amino acetate dichlorohydride

STEP A:

[(1,1-dimethylethoxycarbonyl)-amino]-acetate of 1-[4-hydroxy-3-[(2-thiazolylamino)-carbonyl]-8-(trifluoromethyl)-2-quinolinyl]propyl Using the procedure of Example 5, 12 g of 4-hydroxy-2-(1-hydroxypropyl)-N-(2-thiazolyl)-8-trifluoromethyl-3-quinoline carboxamide and 5.3 g of N-tertbutoxycarbonyl glycine were reacted to obtain 15.8 g of [(1,1-dimethylethoxycarbonyl)-amino]-acetate of 1-[4-hydroxy]-3-[(2-thiazolylamino)-carbonyl]-8-(trifluoromethyl)-2-quinolinyl]-propyl melting at 196° C.

STEP B:

1-[4-hydroxy-3-[(2-thiazolylamino)-carbonyl]-8-(trifluoromethyl)-2-quinolinyl]-propylamino acetate dichlorohydride A mixture of 14 g of the product of Step A, 70 ml of methylene chloride and 42 ml of a 5.75N solution of ethanol in hydrochloric acid was stirred for 18 hours at ambient temperature and the precipitate is filtered, washed with methylene chloride, then with ether and dried under reduced pressure to obtain 13 g of crude product. The latter was dissolved in 125 ml of methanol and crystallized by the addition of 170 ml of ethyl acetate. After separating, washing with ethyl acetate, and drying under reduced pressure, 8.4 g of 1-[4-hydroxy-3-[2-thiazolylamino)-carbonyl]-8-trifluoromethyl)-2-quinolinyl]-propyl amino acetate dichlorohydride melting at 215° C. were obtained.

EXAMPLE 7

1-[4-hydroxy-3-[(2-thiazolylamino)-carbonyl]-8-trifluoromethyl)-2-quinolinyl]-propyl butanoate Using the procedure of Example 5, 8 g of 4-hydroxy-2-(1-hydroxypropyl)-N-(2-thiazolyl)-8-trifluoromethyl-3-quinoline carboxamide and 2 ml of butyric acid were reacted to obtain 7.8 g of 1-[4-hydroxy-3-[(2-thiazolylamino)-carboxyl]-8-trifluoromethyl)-2-quinolinyl]-propyl butanoate melting at 203° C.

EXAMPLE 8

1-[4-hydroxy-3-[(2-thiazolylamino)-carbonyl]-8-(trifluoromethyl)-2-quinolinyl]-propyl-2,2-dimethylpropanoate Using the procedure of Example 5, 5 g of 4-hydroxy-2-(1-hydroxypropyl)-N-(2-thiazolyl)-8-trifluoromethyl-3-quinoline carboxamide and 1.4 g of pivalic acid were reacted to obtain 5.15 g of 1-[4-hydroxy-3-[(2-thiazolylamino)-carbonyl]-8-(trifluoromethyl)-2-quinolinyl]-propyl-2,2-dimethylpropanoate melting at 244° C.

EXAMPLE 9

1-[4-hydroxy-3-(2-thiazolylamino)-carbonyl]-8-(trifluoromethyl)-2-quinolinyl]-propyl dodecanoate Using the procedure of Example 5, 5 g of 4-hydroxy-2-(1-hydroxypropyl)-N-(2-thiazolyl)-8-trifluoromethyl-3-quinoline carboxamide and 2.8 g of lauric acid were reacted to obtain 6 g of 1-[4-hydroxy-3-(2-thiazolylamino)-carbonyl]-8-(trifluoromethyl)-2-quinolinyl]-propyl dodecanoate melting at 158° C.

EXAMPLE 10

1-[4-hydroxy-3-[(2-thiazolylamino)-carbonyl]-8-(trifluoromethyl)-2-quinolinyl]-propyl-3-pyridine carboxylate Using the procedure of Example 5, 5 g of 4-hydroxy-2-(1-hydroxypropyl)-N-(2-thiazolyl)-8-trifluoromethyl-3-quinoline carboxamide and 1.68 g of nicotinic acid were reacted to obtain 4.75 g of 1-[4-hydroxy-3-[(2-thiazolylamino)-carbonyl]-8-(trifluoromethyl)-2-quinolinyl]-propyl-3-pyridine carboxylate melting at 200° C.

EXAMPLE 11

2-[1-(benzyloxy)-propyl]-4-hydroxy-N-(2-thiazolyl)-8-(trifluoromethyl)-3-quinoline carboxamide Using the procedure of Example 5, 5 g of 4-hydroxy-2-(1-hydroxypropyl)-N-(2-thiazolyl)-8-trifluoromethyl-3-quinoline carboxamide and 1.7 g of benzoic acid were reacted to obtain 4.65 g of 2-[1-(benzoyloxy)-propyl]-4-hydroxy-N-(2-thiazolyl)-8-(trifluoromethyl)-3-quinoline carboxamide melting at 230° C.

EXAMPLE 12

1-[4-hydroxy-3-[(2-thiazolylamino)-carbonyl]-8-trifluoromethyl-2-quinolinyl]-propyl-3-phenyl-2-propenoate Using the procedure of Example 5, 5 g of 4-hydroxy-2-(1-hydroxypropyl)-N-(2-thiazolyl)-8-trifluoromethyl-3-quinoline carboxamide and 2.05 g of cinnamic acid were reacted to obtain 4.65 g of 1-[4-hydroxy-3-[(2-thiazolylamino)-carbonyl]-8-trifluoromethyl-2- quinolinyl]-propyl-3-phenyl-2-propenoate melting at 210° C.

EXAMPLE 13

1-[4-hydroxy-3-[(2-pyridinylamino)-carbonyl]-8-(trifluoromethyl)-2-quinolinyl]-propyl propanoate

STEP A:

2-[(2-chloro-1-oxobutyl)-amino]-β-oxo-N-(2-pyridinyl)-3-trifluoromethyl benzene propanamide 314.3 ml of a 1.4M solution of n-butyllithium in hexane were added to a solution of 30 g of 2-acetylamino pyridine in 886 ml of tetrahydrofuran. After cooling to −70° C., a solution of 32 g of 2-(1-chloropropyl)-8-trifluoromethyl-4H-3,1-benzoxazine-4-one [prepared by the process of Example 10 of Belgian Pat. No. 896,941] in 230 ml of tetrahydrofuran was added and the solution was poured into 500 ml of 2N hydrochloric acid and 600 ml of water. The aqueous phase was extracted with ethyl acetate and the combined organic phases were dried and concentrated to dryness under reduced pressure. The residue was taken in ethyl ether, separated and dried to obtain 9.1 g of 2-[(2-chloro-1-oxobutyl)-amino]-β-oxo-N-(2-pyridinyl)-3-trifluoromethyl benzene propanamide melting at 137° C.

STEP B:

1,3-dihydro-3-ethyl-2-[(2-pyridinyl)-amino]-5-trifluoromethyl furo[3,4-b]-quinolin-9-ol A mixture of 27.8 g of the product of Step A and 9.46 g of 4-dimethylamino-pyridine in 500 ml of dioxane was refluxed for 90 minutes and after cooling, eliminating the solvent under reduced pressure, taking up the residue in 300 ml of ethyl ether and separating, the solid was dissolved in a 1-1 mixture of methylene chloride and water. The aqueous phase was extracted with methylene chloride and the combined organic phases were dried and concentrated to dryness under reduced pressure. After taking up the residue with ethyl ether, separating and drying the crystallized product, 14.4 g of 1,3-dihydro-3-ethyl-2-[(2-pyridinyl)-amino]-5-trifluoromethyl furo[3,4-b]-quinolin-9-ol melting at 172° C. were obtained.

STEP C:

1-[4-hydroxy-3-[(2-pyridinylamino)-carbonyl]-8-(trifluoromethyl)-2-quinolinyl]-propyl propanoate A mixture of 6 g of 1,3-dihydro-3-ethyl-2-[(2-pyridinyl)-amino]-5-trifluoromethyl furo[3,4-b]-quinolin-9-ol in 120 ml of propionic acid was refluxed for 5 hours. After cooling and pouring into 150 ml of water, the precipitate was separated, washed with water and dissolved in 300 ml of ethyl acetate and 50 ml of tetrahydrofuran. The organic phase was washed, filtered over active carbon and concentrated to dryness under reduced pressure. The residue was crystallized from ethyl acetate, and after separating and drying, 3.08 g of 1-[4-hydroxy-3-[(2-pyridinylamino)-carbonyl]-8-(trifluoromethyl)-2-quinolinyl]-propyl propanoate melting at 204° C. were obtained.

EXAMPLE 14

1-[4-hydroxy-3-[(2-pyridinyl)-aminocarbonyl]-8-trifluoromethyl-2-quinolinyl]-2-methylpropyl acetate

STEP A:

2-[(2-chloro-3-methyl-1-oxobutyl)-amino]-β-oxo-N-(2-pyridinyl)-3-trifluoromethyl-benzene propanamide Using the procedure of Step A of Example 13, 10.16 g of 2-acetylaminopyridine, 106 ml of a hexane solution of n-butyllithium (1,4M) and 11.4 g of 2-(1-chloro-2-methylpropyl)-8-trifluoromethyl-4H-3,1-benzoxazin-4-one of Step A of example 3 were reacted to obtain 11.8 g of 2-[(2-chloro-3-methyl-1-oxobutyl)-amino]-β-oxo-N-(2-pyridinyl)-3-trifluoromethyl-benzene propanamide melting at 136°–138° C.

STEP B:

1,3-dihydro-3-(1-methylethyl)-1-[(2-pyridinyl)imino]-5-trifluoromethyl furo-[3,4-b]-quinolin-9-ol 10.5 g of the product of Step A and 2.9 g of 4-dimethylamino-pyridine in 100 ml of tetrahydrofuran were refluxed for 7 hours 30 minutes and after cooling, the solvent was eliminated under reduced pressure. The residue was taken up in 100 ml of water and 10 ml of acetone. After separating, washing with water and drying at 70° C. under reduced pressure, 7.8 g of 1,3-dihydro-3-(1-methylethyl)-1-[(2-pyridinyl)-imino]-5-trifluoromethyl furo-[3,4-b]-quinolin-9-ol melting at 178°–180° C. were obtained.

STEP C:

1-[4-hydroxy-3-[(2-pyridinyl)-aminocarbonyl]-8-trifluoromethyl-2-quinolinyl]-2-methylpropyl acetate Using the procedure of Example 13, 6 g of 1,3-dihydro-3-(1-methylethyl)-1-[(2-pyridinyl)-imino]-5-trifluoromethyl furo-[3,4-b]-quinolin-9-ol and 120 ml of acetic acid were reacted to obtain 3.5 g of 1-[4-hydroxy-3-[(2-pyridinyl)-aminocarbonyl]-8-trifluoromethyl-2-quinolinyl]-2-methylpropyl acetate melting at 230° C.

EXAMPLE 15

1-[4-hydroxy-3-[(2-pyridinyl)-aminocarbonyl]-8-trifluoromethyl-2-quinolinyl]-2-methyl-propyl propanoate Using the procedure of Example 13, 5.9 g of 1,3-dihydro-3-(1-methylethyl)-1-[(2-pyridinyl)-imino]-5-trifluoromethyl furo-[3,4-b]-quinolin-9-ol of Example 14 and 120 ml of propionic acid were reacted to obtain 2.7 g of 1-[4-hydroxy-3-[(2-pyridinyl)-aminocarbonyl]-8-trifluoromethyl-2-quinolinyl]-1-methyl-propyl propanoate melting at 192° C.

EXAMPLE 16

4-hydroxy-2-[1-(1-oxopropoxy)-propyl]-N-(2-thiazolyl)-8-trifluoromethyl-3-quinoline carboxamide, isomer A

STEP A:

1-[4-hydroxy-3-[(2-thiazolylamino)-carbonyl]-8-trifluoromethyl-2-quinolinyl]-propyl-α-methoxy benzene acetate, isomers A and B 13.36 g of dicyclohexylcarbodiimide were added to a suspension of 12 g of R(-)methoxyphenylacetic acid, 28.7 g of 4-hydroxy-2-(1-hydroxypropyl)-N-(2-thiazolyl)-8-trifluoromethyl-3-quinoline carboxamide [prepared as in Example 10 of Belgian Pat. No. 896,941] in 280 ml of methylene chloride and after stirring 4.3 g of 4-dimethylamino-pyridine were added. The mixture was stirred for 2 hours and 30 minutes and the dicyclohexylurea formed was filtered off. The organic phase was washed with N hydrochloric acid, then with a saturated aqueous solution of sodium bicarbonate, washed with water, dried and concentrated to dryness under reduced pressure to obtain 44.1 g of crude product. The latter was dissolved in 150 ml of methylene chloride and the insoluble matter was eliminated by filtration. Chromatography over silica and elution with ethyl acetate-hexane (1-1) yielded 15.18 g of isomer A melting at 172° C. and having a specific rotation of $[\alpha]_D = -26° \pm 3°$ (c=0.3%, methylene chloride) and 14.24 g of isomer B melting at 194° C. and having a specific rotation of $[\alpha]_D = -31° \pm 1°$ (c=1%, methylene chloride.

STEP B:
4-hydroxy-2-(1-hydroxypropyl)-N-(2-thiazolyl)-8-trifluoromethyl-3-quinoline carboxamide, isomer A 13.68 g of isomer A of Step A were added to 70 ml of butylamine and the mixture stood at ambient temperature for 24 hours. After diluting with 500 ml of ethyl acetate, washing with 800 ml of 2N hydrochloric acid and then with water, drying and concentrating to drynss, 14.7 g of crude product were obtained. After crystallization from ethyl acetate, 3.61 g of 4-hydroxy-2-(1-hydroxypropyl)-N-(2-thiazolyl)-8-trifluoromethyl-3-quinoline carboxamide, isomer A melting at 180° C. were obtained $[\alpha]_D = -47° \pm 2°$ (c=0.5% in chloroform)

STEP C:
4-hydroxy-2-[1-(1-oxopropoxy)-propyl]-N-(2-thiazolyl)-8-trifluoromethyl-3-quinoline carboxamide, isomer A Using the procedure of Example 6, isomer A of 4-hydroxy-2-(1-hydroxypropyl)-N-(2-thiazolyl)-8-trifluoromethyl-3-quinoline carboxamide was reacted to obtain 4-hydroxy-2-[1-(1-oxopropoxy)-propyl]-N-(2-thiazolyl)-8-trifluoromethyl-3-quinoline carboxamide, isomer A melting at 187° C. and having a specific rotation of $[\alpha]_D = -9.5° \pm 1.5°$ (c=0.7% in acetone).

EXAMPLE 17
4-hydroxy-2-[1-(1-oxopropxy)-propyl]-N-(2-thiazolyl)-8-trifluoromethyl-3-quinoline carboxamide, isomer B

STEP A:
4-hydroxy-2-(1-hydroxypropyl)-N-(2-thiazolyl)-8-trifluoromethyl-3-quinoline carboxamide isomer B Using the procedure of Step B of Example 16, 12.14 g of isomer B of 1-[4-hydroxy-3-[(2-thiazolylamino)carbonyl]-8-trifluoromethyl-2-quinolinyl]-propyl α-methoxy benzene acetate [prepared by the process of Step A of Example 16] were reacted to obtain 3.18 g of 4-hydroxy-2-[1-hydroxypropyl]-N-(2-thiazolyl)-8-trifluoromethyl-3-quinoline carboxamide isomer B melting at 180° C. and having a specific rotation of $[\alpha]_D = +54° \pm 2.5°$ (c=0.5% in chloroform) and $[\alpha]_D = -51.5° \pm 2.5°$ (c=0.7% in acetone).

STEP B:
4-hydroxy-2-[1-(1-oxopropoxy)-propyl]-N-(2-thiazolyl)-8-trifluoromethyl-3-quinoline carboxamide, isomer B Using the procedure of Example 6, isomer B of 4-hydroxy-2-[1-hydroxy-2-(1-hydroxypropyl)]-N-(2-thiazolyl)-8-trifluoromethyl-3-quinoline carboxamide was reacted to obtain 4-hydroxy-2-[1-(1-oxoproxy)-propyl]-N-(2-thiazolyl)-8-trifluoromethyl-3-quinoline carboxamide, isomer B melting at 187° C. and having a specific rotation of $[\alpha]_D = +8.5° \pm 1.5°$ (c=0.5% in acetone).

EXAMPLE 18

Tablets were prepared containing 50 mg of the product of Example 2 or 7 and sufficient excipient of lactose, talc, starch, magnesium stearate for a final tablet weight of 350 mg.

PHARMACOLOGICAL STUDY

A. Anti-inflammatory activity: chronic arthritis of adjuvant (preventive treatment)

The injection of adjuvant of "Freund" type into a hind paw causes in rats the rapid appearance of a primary inflammatory lesion in this paw and then after a latent period of 13 to 15 days, causes a secondary arthritis affecting in particular the other hind paw. The test was carried out on male rats aged from 42 to 50 days which received by intraplantar injection 0.1 ml of adjuvant of "Freund" type (suspension in vaseline oil of 6 mg per ml. of killed mycobacterium butyricum). The animals received the product studied orally for day 0 (day of the injection of the adjuvant) until the day before they were killed which occurred on day 17. The arthritic control animals and normal control animals received only the vehicle. The assessment criteria of the activity of the substances studied were the increase in the volume of hind paws injected (primary and secondary inflammation) and not injected (secondary inflammation) in comparison with the average volume of paws corresponding to the normal controls. The $DA_{50}$ was determined, that is to say the dose which reduced the increase in volume of the hind paws of the treated animals in comparison to those of the control animals by 50%. The following results were obtained:

| Product of Example | $DA_{50}$ in mg/kg |
| --- | --- |
| 2 | 0.8 |
| 7 | 1.3 |
| 6 | 1.0 |

* Gastric ulceration effect

The test was done on female rates weighing 120 to 150 g on a water diet for 24 hours at the time of the treatment divided into random groups. The products were administered orally and seven hours later, the animals were killed and their stomachs opened along the great curvature, washed in an isotonic solution of sodium chloride and spread apart by wiping with a cotton pad soaked in the same solution. The degree of ulcerous lesions, in number and in size, was estimated on a scale from 0 to 3 by two observers unware of the treatments. The notation 1 indicated the presence of an obvious ulcer or of several punctiform ulcers.

To take in account also the percentage of rats having ulcers (degree of ulceration greater than 0.5, notation attributed to a hyperemia or to petechiae often encountered in a control which had fasted) an ulceration index was calculated for each group according to the formula $$\frac{\text{Degree of ulceration} \times \text{number of rats having an ulcer}}{\text{number of rats}} \times 100$$

The dose corresponding to an ulceration index of 100 or DU 100 was graphically determined (the maximum ulceration index is 300). The DU 100 was found to be greater than 300 mg/kg for the products of Examples 2 and 7.

Various modifications of the compounds and method of the invention may be made without departing from the spirit or scope thereof and it is to be understood that the invention is intended to be limited only as defined in the appended claims.

What we claim is:

1. A compound selected from the group consisting of optical isomers and racemates of 4-hydroxy-3-quinoline-carboxylates of the formula

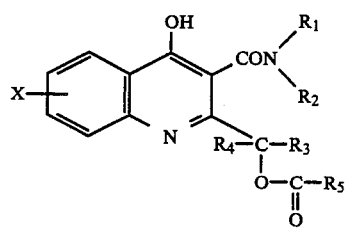

wherein X is in the 5-, 6-, 7- or 8-position and is selected from the group consisting of hydrogen, halogen, alkyl of 1 to 5 carbon atoms, alkoxy of 1 to 4 carbon atoms, $-CF_3$, $-SCF_3$ and $-OCF_3$, $R_1$ is selected from the group consisting of hydrogen and alkyl of 1 to 4 carbon atoms, $R_2$ is selected from the group consisting of thiazolyl, 4,5-dihydrothiazolyl, pyridinyl, oxazolyl, isoxazolyl, imidazolyl, pyrimidyl and tetrazolyl, all optionally substituted with alkyl of 1 to 4 carbon atoms and phenyl and phenyl substituted with at least one member of the group consisting of $-OH$, alkyl and alkoxy of 1 to 4 carbons atoms, $-CF_3$, $-NO_2$ and halogen, $R_3$ and $R_4$ are individually selected from the group consisting of hydrogen, alkyl of 1 to 4 carbon atoms, phenyl and naphthyl, $R_5$ is selected from the group consisting of phenyl, naphthyl, pyridyl alkyl of 1 to 14 carbon atoms, alkyl substituted with $-NH_2$, $-NHAlk$ or

alkenyl of 2 to 6 carbon atoms, alkenyl of 2 to 6 carbon atoms with phenyl or naphthyl, Alk and Alk' are alkyl of 1 to 6 carbon atoms and their non-toxic, pharmaceutically acceptable acid addition salts with the proviso that when X is 8-$CF_3$, $R_1$ and $R_3$ are hydrogen, $R_2$ is 2-thiazolyl, $R_4$ is methyl, $R_5$ is not methyl.

2. A compound of claim 1 wherein X is 8-$CF_3$ and its non-toxic, pharmaceutically acceptable acid addition salts.

3. A compound of claim 1 wherein $R_1$ is hydrogen and its non-toxic, pharmaceutically acceptable acid addition salts.

4. A compound of claim 1 wherein $R_3$ is hydrogen and its non-toxic, pharmaceutically acceptable acid addition salts.

5. A compound of claim 1 wherein $R_2$ is thiazolyl and its non-toxic, pharmaceutically acceptable acid addition salts.

6. A compound of claim 1 wherein $R_4$ is ethyl and $R_5$ is selected from the group consisting of alkyl of 1 to 4 carbon atoms and alkyl of 1 to 4 carbon atoms substituted by an amino radical and their non-toxic, pharmaceutically acceptable acid addition salts.

7. A compound of claim 1 selected from the group consisting of 2-[1-(1-oxo-propoxy)-propyl]-4-hydroxy-N-(2-thiazolyl)-8-trifluoromethyl)-3-quinoline carboxamide, in racemic or optically active form, 2-[1-(1-oxobutoxy)-propyl]-4-hydroxy-N-(2-thiazolyl)-8-(trifluoromethyl)-3-quinoline carboxamide, in racemic or optically active form and, 2-[1-(1-oxo-2-aminoethoxy)-propyl]-4-hydroxy-N-(2-thiazolyl)-8-(trifluoromethyl)-3-quinoline carboxamide, in racemic or optically active forms, and their non-toxic, pharmaceutically acceptable acid addition salts.

8. An analgesic composition comprising an analgesically and an anti-inflammatorily effective amount of at least one compound of claim 1 and an inert pharmaceutical carrier.

9. A composition of claim 8 wherein X is 8-$CF_3$ and its non-toxic, pharmaceutically acid addition salts.

10. A composition of claim 8 wherein $R_1$ is hydrogen and its non-toxic, pharmaceutically acceptable acid addition salts.

11. A composition of claim 8 wherein $R_3$ is hydrogen and its non-toxic, pharmaceutically acceptable acid addition salts.

12. A composition of claim 8 wherein $R_2$ is thiazolyl and its non-toxic, pharmaceutically acceptable acid addition salts.

13. A composition of claim 8 wherein $R_4$ is ethyl and $R_5$ is selected from the group consisting of alkyl of 1 to 4 carbon atoms and alkyl of 1 to 4 carbon atoms substituted by an amino radical and their non-toxic, pharmaceutically acceptable acid addition salts.

14. A composition of claim 8 wherein the active ingredient is selected from the group consisting of 2-[1-(1-oxopropoxy)-propyl]-4-hydroxy-N-(2-thiazolyl)-8-(trifluoromethyl)-3-quinoline carboxamide, in racemic or optically active form, 2-[1-(1-oxobutoxy)-propyl]-4-hydroxy-N-(2-thiazolyl)-8-(trifluoromethyl)-3-quinoline carboxamide, in racemic or optically active form and, 2-[1-(1-oxo-2-aminoethoxy)-propyl]-4-hydroxy-N-(2-thiazolyl)-8-(trifluoromethyl)-3-quinoline carboxamide, in racemic or optically active forms and their non-toxic, pharmaceutically acceptable acid addition salts.

15. A method of treating pain and inflammation in warm-blooded animals comprising administering to warm-blooded animals an anaglesically and anti-inflammatorily effective amount of at least one compound of claim 1.

16. A method of claim 15 wherein in the compound X is 8-$CF_3$ and its non-toxic, pharmaceutically acceptable acid addition salts.

17. A method of claim 1 wherein in the compound $R_1$ is hydrogen and its non-toxic, pharmaceutically acceptable acid addition salts.

18. A method of claim 15 wherein in the compound $R_3$ is hydrogen and its non-toxic, pharmaceutically acceptable acid addition salts.

19. A method of claim 15 wherein in the compound $R_2$ is thiazolyl and its non-toxic, pharmaceutically acceptable acid addition salts.

20. A method of claim 15 wherein in the compound $R_4$ is ethyl and $R_5$ is selected from the group consisting of alkyl of 1 to 4 carbon atoms and alkyl of 1 to 4 carbon atoms substituted by an amino radical and their non-toxic, pharmaceutically acceptable acid addition salts.

21. A method of claim 15 wherein the compound is selected from the group consisting of 2-[1-(1-oxo-propoxy)-propyl]-4-hydroxy-N-(2-thiazolyl)-8-(trifluoromethyl)-3-quinoline carboxamide, in racemic or optically active form, 2-[1-(1-oxobutoxy)-propyl]-4-hydroxy-N-(2-thiazolyl)-8-(trifluoromethyl)-3-quinoline carboxamide, in racemic or optically active form and, 2-[1-(1-oxo-2-amino-ethoxy)-propyl]-4-hydroxy-N-(2-thiazolyl)-8-(trifluoromethyl)-3-quinoline carboxamide in racemic or optically active forms and their non-toxic, pharmaceutically acceptable acid addition salts.

* * * * *